(12) United States Patent
Fischer

(10) Patent No.: US 11,331,510 B2
(45) Date of Patent: May 17, 2022

(54) DEVICE FOR MAGNETIC FIELD STIMULATION OF THE BODY TISSUE OF A USER FOR USE IN DIGITAL TELEMEDICINE, IN PARTICULAR ACCORDING TO THE E-PULSE METHOD FOR PELVIC FLOOR OPTIMIZATION

(71) Applicant: Prof. Dr. Fischer AG, Eschen (LI)

(72) Inventor: Gerhard Fischer, Heerbrugg (CH)

(73) Assignee: PROF. DR. FISCHER AG, Eschen (LI)

( * ) Notice: Subject to any disclaimer, the term of this patent is extended or adjusted under 35 U.S.C. 154(b) by 0 days.

(21) Appl. No.: 16/985,677

(22) Filed: Aug. 5, 2020

(65) Prior Publication Data

US 2021/0052911 A1    Feb. 25, 2021

(30) Foreign Application Priority Data

Aug. 5, 2019   (DE) ..................... 10 2019 121 072.0

(51) Int. Cl.
| | |
|---|---|
| *A61N 2/00* | (2006.01) |
| *A61N 2/02* | (2006.01) |
| *G06F 3/041* | (2006.01) |
| *G06F 3/16* | (2006.01) |

(52) U.S. Cl.
CPC ............. *A61N 2/004* (2013.01); *A61N 2/02* (2013.01); *G06F 3/041* (2013.01); *G06F 3/167* (2013.01)

(58) Field of Classification Search
CPC .......... A61N 2/00; A61N 2/002; A61N 2/004; A61N 2/006; A61N 2/008; A61N 2/02
See application file for complete search history.

(56) References Cited

U.S. PATENT DOCUMENTS

| | | | |
|---|---|---|---|
| 8,958,882 B1* | 2/2015 | Hagedorn | A61B 5/0006 607/45 |
| 10,773,094 B1* | 9/2020 | Rzasa | G06K 19/0723 |
| 2002/0165583 A1 | 11/2002 | Tepper et al. | |
| 2006/0145457 A1* | 7/2006 | Prenzel | B64D 11/00155 280/735 |
| 2018/0345833 A1* | 12/2018 | Gallagher | A61B 5/1114 |

FOREIGN PATENT DOCUMENTS

| | | |
|---|---|---|
| CN | 109381790 A | 2/2019 |
| DE | 29808990 U1 | 8/1998 |
| DE | 102004058722 A1 | 6/2006 |

(Continued)

*Primary Examiner* — Samuel G Gilbert
(74) *Attorney, Agent, or Firm* — Browdy and Neimark, PLLC

(57) ABSTRACT

A device for magnetic field stimulation of a user's body tissue, is provided which includes an adjustable seating arrangement for the user, at least one magnetic field applicator for generating a pulsating magnetic field in the area of the seating arrangement, control panel for setting one or several parameters of the pulsating magnetic field comprising pulse duration, pulse frequency and pulse amplitude, and/or for adjusting the seating arrangement, and display screen for displaying information. The control panel are designed to manually and/or automatically adjust one or more of the parameters of the magnetic field and/or to adjust the seating arrangement as a function of previously recorded individual information about the user.

12 Claims, 1 Drawing Sheet

(56) References Cited

FOREIGN PATENT DOCUMENTS

| | | |
|---|---|---|
| DE | 202009013768 U1 | 2/2011 |
| DE | 102017122942 A1 | 4/2019 |
| DE | 102017123854 A1 | 4/2019 |
| EP | 2676700 A | 12/2013 |
| JP | 2002-522125 A | 7/2002 |
| KR | 102016044184 A | 4/2016 |
| RU | 2158616 C2 | 11/2000 |
| WO | 2014091457 A2 | 6/2014 |

* cited by examiner

DEVICE FOR MAGNETIC FIELD STIMULATION OF THE BODY TISSUE OF A USER FOR USE IN DIGITAL TELEMEDICINE, IN PARTICULAR ACCORDING TO THE E-PULSE METHOD FOR PELVIC FLOOR OPTIMIZATION

The invention relates to a device for magnetic field stimulation of body tissue of a user, in particular according to the E-pulse method for pelvic floor optimization. The device for magnetic field stimulation is particularly suitable for use in digital telemedicine.

The device is used to stimulate motor neurons and the reflex arc by afferents of the peripheral nervous system in order to cause pelvic skeletal muscles to contract and to relax the detrusor vesicae muscle. The device is designed in particular for the treatment of pelvic floor weakness and associated incontinence symptoms, irritation of the bladder and for the treatment of erectile dysfunctions in blood flow-related disorders. It is also designed for a large number of prophylactic and therapeutic applications in the physiotherapeutic, orthopedic and dermatological fields.

DE 298 08 990 U1 discloses seating and reclining furniture for magnetic field therapy, which furniture has one or more applicator devices for generating magnetic fields. The applicator device can be embedded in the upholstery of the respective seating or reclining furniture. Furthermore, the applicator device for generating magnetic fields can be equipped with coils, which enables whole-body or partial-body therapy with full-core metal coils arranged in rows or in a circle.

DE 10 2017 122 942 A1 relates to a relaxation couch for relaxing and/or therapeutic treatment of a user, with a lying surface which has a seat surface, a backrest and a leg rest, wherein means for generating a magnetic oscillation field in the region of the lying surface and means for generating a weighing movement and/or rocking movement of the lying surface are included.

It is the object of the present invention to provide a device for magnetic field stimulation which allows a comfortable and user-specific magnetic field treatment.

The device for magnetic field stimulation of a user's body tissue comprises an adjustable seating arrangement for the user, at least one magnetic field applicator for generating a pulsating magnetic field in the region of the seating arrangement, adjusting means for adjusting one or more parameters of the pulsating magnetic field including pulse duration, pulse frequency and pulse amplitude, and/or adjusting the seating arrangement, and display means for displaying information.

According to the invention, the adjusting means are designed to manually and/or automatically adjust one or more of the parameters of the magnetic field and/or to adjust the seating arrangement depending upon previously recorded individual information about the user.

The magnetic field applicator comprises a programmable pulse generator, of which the pulse duration, pulse frequency and pulse amplitude can be adjusted. The pulse generator generates low-frequency pulses, preferably in the range of 1-100 Hz, and is connected to one or more magnetic coils 15, which generate a pulsating magnetic field in the seat surface and/or the backrest and/or the foot part of the seating arrangement.

In a preferred embodiment of the invention, the adjustment of the seating arrangement and/or the adjustment of the pulsating magnetic field are carried out automatically on the basis of the information available about the user.

To determine which user would like to use the device, in a preferred embodiment of the invention it is provided that a device for automatic recognition of the user is present. The user can be identified optically and/or acoustically, for example by face recognition using a camera, fingerprint recognition or voice recognition or a combination of these methods. Another possibility is to identify user identity information in the form of a chip card, an RFID chip or the like.

Furthermore, it is provided according to the invention that adjustment means for inputting and/or reading out individual information about the user are available, the information comprising in particular information about the physical characteristics and/or the state of health of the user. These adjusting means can optionally include a keyboard and/or a touchscreen and/or a device for voice input.

In another preferred embodiment of the invention, the individual information of the current user is compared with information from other users, and the parameters of the magnetic field for the current user are adjusted taking into account the parameters set for other users. In other words, a magnetic field treatment successfully carried out on other users is also carried out on the current user with a similar diagnosis or complaints.

The user can be shown information on the effect of different settings of the pulsating magnetic field on the body tissue on the display means. In particular, the information can also relate to individual indications that can be treated with the device, and the most complex urological and gynecological changes and deficiencies of the pelvic floor, the bladder and the bladder sphincter system can be explained in a clear and concise manner In a particular embodiment of the invention, a device for generating illumination and light effects is provided in order to improve the well-being of the user during the treatment and to increase the success of the treatment.

An infotainment system for playing music, sounds and sound effects can also be provided, which serves for information and the well-being of the user.

A microphone can also be provided for recording voice information for voice control and/or for recognizing the user (voice recognition).

The operating device can have a keyboard and/or a touch-sensitive display device (touchscreen).

The personal information recorded by the user is preferably stored and evaluated in the device itself and/or also in a control center. The center can be a telemedical center, which evaluates the user data and, if desired, provides supporting information for the treatment of the user. The device for magnetic field treatment is connected to the control center via a communication system.

Furthermore, in a preferred development of the invention, grab handles for the user are provided in the region of the seating arrangement. This enables the user to actively tense his muscles during treatment and to increase the success of the treatment.

A preferred embodiment of the invention is described below with reference to the drawing figures. Further features and advantages of the invention are apparent from the drawings and their description.

Figure 2:
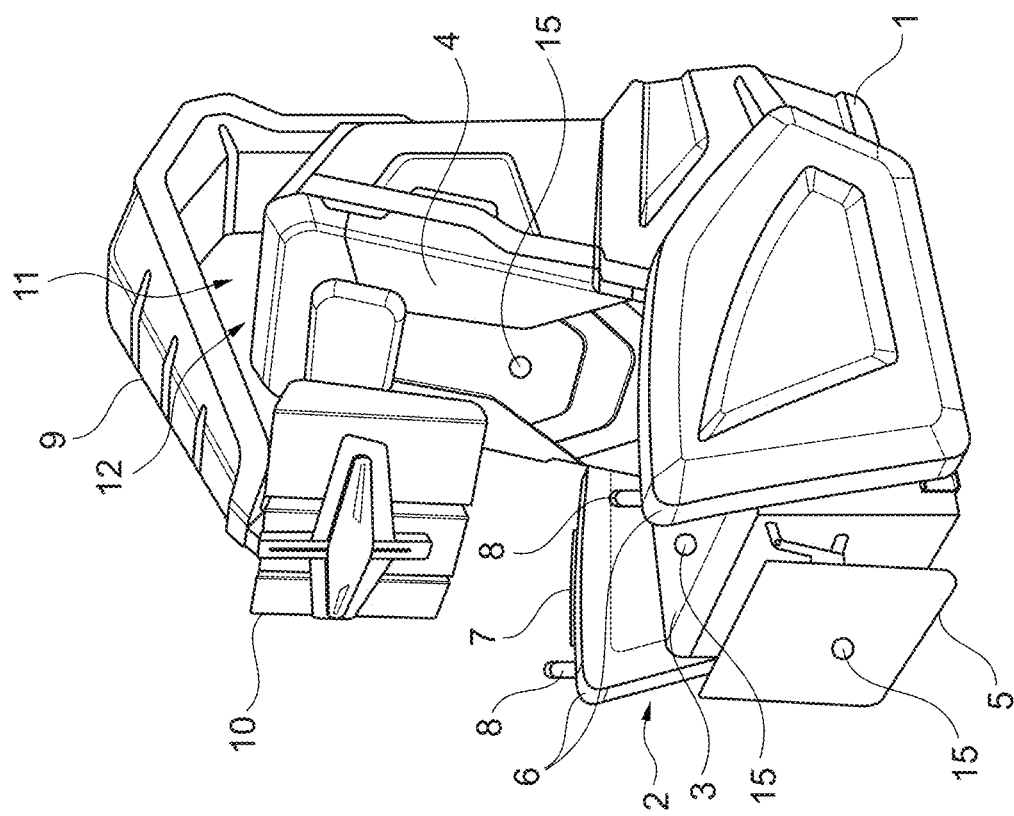
FIG. 2 shows a perspective front view of the magnetic stimulation device.
Figure 1:
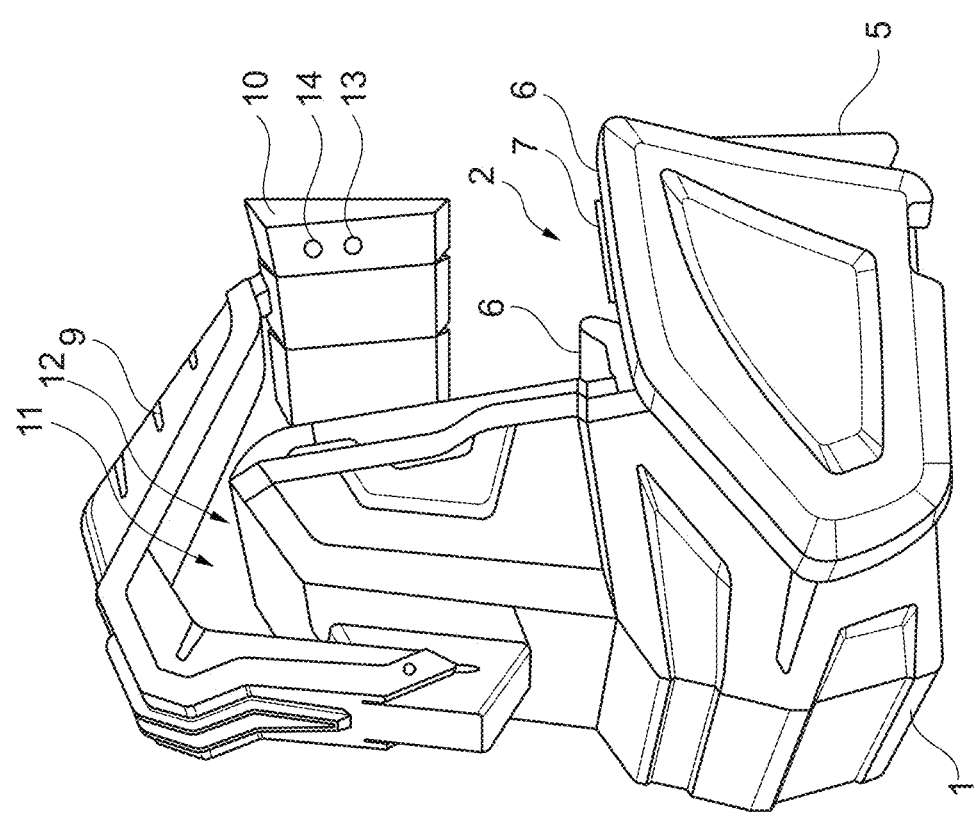
FIG. 1 shows a perspective side view of the magnetic stimulation device.

The device for magnetic field stimulation according to FIGS. 1 and 2 comprises a base frame 1, on which a seating arrangement is mounted, for example in the form of a comfortable, adjustable armchair 2. The design of the device for magnetic field stimulation according to the invention is irrelevant to the function of the invention and is only intended to be shown here by way of example. Furthermore, some of the existing technical facilities are only shown schematically.

The seating arrangement 2 comprises a seat surface 3, a backrest 4 and a foot part 5, which are adjustable so that the user can assume a sitting or lying position that is comfortable for him. The seating arrangement 2 is adjusted manually or automatically via a control panel 7 based on a sitting or lying position previously saved and retrievable by the user. Furthermore, the seating arrangement 1 comprises an armrest 6, the control panel 7 being arranged on one or both armrests 6. The control panel 7 is equipped with a keyboard and/or a touchscreen.

The device preferably has a light hood 9. An infotainment system for playing music, sounds and sound effects and light effects is provided in or on the light hood 9. The infotainment system comprises at least one integrated screen 10 in the user's field of vision, a microphone 13, loudspeaker 11 or a Bluetooth headset with an integrated microphone and illuminating means 12. A camera 14 directed at the user can also be provided. These devices are used not only for communication with an (external) telemedical center, but also for supporting treatment information for the user, correct implementation of "high mental effort training" and as a multi-purpose infotainment system.

The device for magnetic field stimulation preferably comprises a plurality of functional modules which facilitate the various functions of the device. The functional modules can be selected by the user and support, supplement and improve treatment of the user with the magnetic stimulation device. The functional modules of the magnetic stimulation device are connected via the devices of the infotainment system, in particular the control panel 7, screen 10, loudspeaker 10, microphone 13 and camera in connection with and/or in dialogue with the user and the control center.

Infotainment Module

This information and entertainment module is aimed primarily at rPMS users for whom high mental effort training is out of the question. Since the training lasts up to 20 minutes, this time is used in subsequent sessions to provide the user with information about urinary or fecal incontinence, sarcopenia and the risk of falling, or facts about performance improvement. In particular sarcopenia, in which the loss of muscle mass already begins in the 4th decade of life and accelerates up to 3% annually between the 50th and 80th year of life, and which is primarily based on a breakdown of the alpha motor neurons of the spinal ganglion, but also on the decoupling of motor units or the infiltration of connective and adipose tissue, is a serious aging phenomenon. The decrease in skeletal muscle strength mainly only affects the breakdown of fast muscle fibers (fast-twitch fibers). A decrease in muscle mass and muscle strength particularly affects the lower extremities, which is all the more serious because walking is one of the essential necessities of everyday life and also affects the core. As a result, this power distribution box is not only the stabilizing element for all physical actions, but is also essential for equilibrium and the ability to balance. If the gait is unsafe, however, the risk of falling and thus the mortality risk increases (Freiberger E., Sieber C., Pfeifer K. Physical activity, exercise, and sarcopenia—future challenges. Wien Med Wochenschr. 2011; 161 (17-18): 416-425). Falls and fractures are the most common cause of death in people over 65 years of age or often require subsequent admission to a home, which is all the more worrying given that 25.7% of all women between the ages of 65 and 79 years need medical treatment for a fall.

Therefore, rPMS is not only important in the treatment of urinary incontinence, myofascial pain syndrome, sexual dysfunction or the improvement of athletic performance. Rather, it offers the opportunity to stop the age-related muscle loss of the dominant walking muscles and the associated disturbance of the ability to balance without any effort.

With the infotainment system, however, the operator (user/athlete) is also informed about the additional benefit of specific substrates, which relate to the training physiology and the optimal nutritional requirements of intensive muscle training. For example, there are findings on the improvement in performance through acid buffering in the case of the short-term lactic acid loads present here or also repetitive, high-intensity loads through the supplementation of a certain dipeptide. A user would also be interested in how the use of so-called BCAA (Branched-Chain Amino Acids) in the "resistance training" simulated here with the rPMS should be assessed, or the importance of break times during the rMPS treatment.

If an rPMS focuses primarily on fat loss (e.g. also visceral fat), it is important for the user to learn, for example, how the liver can be forced to burn fat by activating PPARa (Peroxisome Proliferator Activated Receptor alpha). If rPMS is about erectile dysfunction (impotence)—unlike female sexual dysfunction—animated sexual film content should be avoided.

However, infotainment is not limited only to health-related information, it also provides other information, such as information about the weather, business news and breaking news/newsflashes.

Face Recognition

The magnetic field stimulation device according to the invention is equipped via a screen 10 and a camera 14 with face recognition software, by means of which the necessary user data as well as names and relationships from previous conversations (e.g. favorite drink, coffee with or without milk and sugar, name of the children, their upcoming class work, marriage, name of the dog, the cat etc.) are available to the practitioner in the display at the beginning of the user settings. The face recognition or the AI also offers the possibility of greeting the user personally based on language software, to inquire about their well-being or to address them about their good appearance etc. Also, the farewell by the language software does not consist of the usual phrases, but from an individual witty farewell greeting—always dependent on the clinical picture, the pain situation, the reason for sexual dysfunction or sporting ambitions.

The background to this personal addressing of the user by the device is the high prevalence of incontinence combined with depressive symptoms (20.6%-43.0%) (Avery J., Stocks N.: Urinary incontinence, depression, and psychosocial factors—a review of population studies. EMJ. 2016; 1(1): 58-67), which can be influenced by a personal address and an associated "attentiveness."

Sound System

A sound system with loudspeakers 11 is installed on both sides in the light hood 9 of the device, and not only offers a unique sound experience, but is also used after the face recognition or user recognition to play a piece of music preferred by the user in a short sequence. Or it opens up the possibility of creating a treatment scenario from a mix of deep vibrating tones as a mood remedy.

Control Panel/Touchscreen

The control panel 7 with touchscreen consists of a swiveling (360 degrees) screen placed vertically on the right armrest of the device, which not only allows the therapist to program the treatment process, but also offers the user the possibility of interrupting the treatment by tapping with the fingertip or querying the remaining treatment time. It also contains an "emergency button," which can be used to notify the therapist if the user is unwell or suffers any other undesirable effects. As an alternative or in addition to the touchscreen, an input keyboard can be provided.

Depending on whether the device is operated by a doctor or by a treatment center managed by doctors or by a physiotherapist on the basis of a doctor's prescription and it is not just a purely sporting or prophylactic pelvic floor training session, the touchscreen program decides on the data protection access authorization for retrieval or electronic forwarding of user and treatment data stored there. This is done by entering an electronic key, which is only available after prior consent from the user.

Telemedicine Module

The device is particularly suitable for use in digital telemedicine. A telemedical center consulted by the device in the first session of the user collects a medical history of the user by means of a digital questionnaire (tablet version) tailored to the combination of findings (urology/gynecology), which is compared by software with data already collected from other previous users. In the event of unusual findings, the system signals further inquiry and checks previous prescription decisions for conformity or collision with the specific treatment recommendation. If the treatment recommendation concerns device-related pelvic floor training using repetitive peripheral magnetic field stimulation (rPMS), the user is informed of a digitized declaration of consent regarding possible contraindications and side effects of the treatment. The same applies to a release from medical confidentiality, so that the operator of the physical pelvic floor training can make the appropriate device settings. Regardless of this, the user has the option of receiving medical advice from a doctor about important treatment questions or unexpected side effects at any time.

Treatment Information Module

The treatment information module which is available for the first treatment sessions is composed of a large number of animation sequences that relate to the individual indications that can be treated with the device and that clearly and concisely explain the mostly complex urological and gynecological changes and deficiencies of the pelvic floor, the bladder and the bladder sphincter system. These are presented to the user by the infotainment system. Based on this, the user should be able to understand—almost at the same time as the real actions of repetitive peripheral magnetic field stimulation (rPMS)—the active principle behind the treatment and what the healing or remission of the disorder is based on.

Thus, the user with stress incontinence learns how, for example, an increase in the muscle strength of the pelvic floor naturally pulling the urethra in the direction of the pubic bone ("integral theory according to Petros"), which— comparable to surgical incontinence treatment using TVT/ TOT—results in a natural bent closure of the urethra, wherein the representation center of the central nervous system (CNS) activated by muscle contractions strengthens the sustainability of the treatment result. Users with an overactive bladder (OAB syndrome) or urge incontinence can in turn understand how the irritation and emptying status of the bladder can be reduced by blocking the pathways of the emptying center in the CNS. Or incontinent users who have undergone a radical prostatectomy learn how important it is to integrate the pelvic floor into the OP-damaged bladder sphincter system using rPMS and thus to compensate for the deficiency. Users with erectile dysfunction (impotence) are brought closer to the importance of the "continence muscle," ischiocavernosus muscle, and why it can be used to prevent a penile venous drainage disorder ("venous leak"). Also, users with hip arthrosis, pelvic pain syndrome, pubic inflammation or lumbar back pain/intervertebral disc events learn how an rPMS-related resolution of the mostly myofascial background can lead to a significant reduction of pain.

With a prevalence of 40-45%, sexual dysfunction is one of the most common diseases affecting women, but often not taken seriously. Above all, "lack of desire" (64%) and "anorgasmia" (35%) are mentioned, followed by problems with sexual arousal and pain during sexual intercourse. Although partner problems, social conditions, childbirth consequences or an estrogen deficiency play a not insignificant role in menopause, a "strong pelvic floor" seems to be essential for pleasure and the ability to achieve orgasm. Here the main focus is on the pubococcygeus muscle (MPC) and iliococcygeus muscle (MICC), since they are also responsible for the vaginal sensation of pleasure and the rhythmic contractions during orgasm. By rPMS training of the pubo- and iliococcygeus muscles, women with orgasm problems become aware of how important this pelvic floor muscle is for their climax.

There are indications that pelvic floor training (cone training) in anorgasmic syndrome gives a better result if women are encouraged to indulge in subjective thoughts of sexual content during the training. Accordingly, an rPMS training of the pubococcygeus and iliococcygeus muscles should not be accompanied by prosaic information about these muscles, but rather with animated sexual sequences that have to be created in comparison with sex therapy findings on fantasies favored by women.

Training Information Module

The core or core strength is one of the most important findings of current sports medicine and training methodology (Hibbs A., Thompson KG., French D. N. et al.: Optimizing Performance by improving Core Stability and Core Strength. Sports Med. 2008; 38 (12): 995-1008). This is because the power transmission between the lower and the upper extremities or the associated technique and precision of a punching, throwing or kicking movement is inseparable from the balancing of an imaginary "muscular box" of the pelvis and the trunk ("proximal stability for distal mobility"). The core consists of the diaphragm, the abdominal muscles, the deep lower back muscles and the multi-layered muscular system of the pelvic floor. However, while a variety of training options are available for the abdominal, pelvic, diaphragm and deep back muscles, exercise approaches such as Pilates, yoga, or the "rubber band-assisted waddling gait" can only insufficiently train the actual pelvic floor. Thus, the trunk and pelvic muscles usually experience an impressive performance gain, but an insufficiently trained pelvic floor leads to a dangerous disparity in the muscular balance and coordination ability as well as to unwanted technical deficiencies and overloading in the distal muscles performing the exercises. The actual goal of reducing the frequency of injuries in the sports of soccer, football, rugby, volleyball, volleyball, golf, tennis, hockey, running sports, etc. is difficult to achieve because only a fully trained core is capable of reducing the effort to be used in the extremities to a minimum (Leetun D. T. et al.:

Core stability measures as risk factors for lower extremity injury in athletes. Med Sci Sports Exerc 2004: 36: 926-934).

An athlete, whether from competitive, club or ambitious mass sports, is able not only to make the myofascial chains visible by means of animated images, but also to show why the power transmission from the extremities or the trunk can only take place via the center (core strength). He is also able to show how the rPMS-related increase in power and coordination of the core enables the transmission of power between the lower and upper extremities to be optimized. This is the only way that an 8-week core strength training session can reduce the susceptibility to injuries by 42% or can reduce the rehabilitation time after an injury by 62% (Peate W. F., Bates G., Lunda K. et al.: Core strength: A new model for injury prediction and prevention. J Occupat Med Toxicol 2007: 2: 3).

High Mental Effort Training Module

A large number of studies have now shown that mental training not only leads to better performance (Feltz D. L., Landers D. M.: The effects of mental practice on motor skill learning and performance: a meta-analysis. J Sports Psychol. 1983; 5: 25-27), but can also initiate significant muscle growth with concentrated visualization (Corbin C. B.: Mental practice. In: Morgan MP. (Ed.): Ergogenic aids and muscular performance. 1972: pp. 93-118: New York, Academic Press). A purely mental 12-week training session (15 minutes/day) succeeded in increasing muscle strength by up to 35% (Ranganathan V. K., Siemionow V., Liu J. Z. et al.: From mental power to muscle-power—gaining strength by using mind. Neurophysiologia. 2004; 42 (7): 944-956). This also results in an enlargement of the corresponding cortical representation in the precentral gyrus of the somatosensory cortex (cerebral cortex), i.e. the representation center for activities of the corresponding muscle group in the periphery of the body, which takes place not only through mental stimulation, but also through proprioceptive feedback after unconscious control and corresponding reaction of the muscles addressed. This is particularly important for the sustainability and retention time of the muscle strengthening that is achieved, since every natural muscle contraction is subject to an increased central signaling and thus more muscle fibers can be addressed. It is thus possible to counteract the increasing decoupling of motor units from the neural supply, which is common in old age (Hughes V. A., Frontera W. R., Wood M. et al.: Longitudinal muscle strength changes in older adults: influence of muscle mass, physical activity, and health. J Geontol Biol Sci Med Sci. 2001; 56 (5): B209-217).

In order to use the full potential of a "passive" rPMS training, it is necessary on the basis of a specific "visualization protocol" to accompany the rPMS-related contraction series of the pelvic floor muscles by the attempt at self-contraction, wherein the user is encouraged to imagine a strong muscle load on the pelvic floor. Self-contraction during rPMS training is a frustrating effort, since the electromagnetically induced action potentials prevent self-contraction. However, a correctly performed visualization leads to an expanded imprint in the representation center in the cerebral cortex by additionally activating and reinforcing "silent" and inhibited synaptic connections there.

High mental effort training (HMET) is particularly effective when a person trains with an MVC (maximum voluntary contraction) of 30% that is too low (Jiang C. H. et al.: The level of effort, rather than muscle exercise intensity determines strength gain following a six-week training. Life Sci. 2017; 178: 30-34), especially since individual, rPMS-enforced muscle contractions are not limiting for stimulation using HMET. This above all benefits people who are not ready to carry out rPMS training of higher intensity due to age or sensitivity. If this means that only parts of the pelvic floor are covered by the rPMS, the global muscle contraction that is so important for muscle growth and central perception is omitted. If a low-intensity rPMS is instead combined with HMET, it is possible to compensate almost completely for the intensity deficiency.

The visualization programs do not refer to a general contraction of the pelvic floor, but differ according to the respective indication. For example, an HMET for stress incontinence is subject to the threat of an impending incontinence situation during physical stress, while in the case of urge incontinence or OAB the mental focus is on blocking the emptying stimulus. Pain syndromes in turn are based on the dissolution of myofascial hardening (taut band) and muscular nodes. Also, the visualization during core strength training is based on the typical movement sequence in the respective sport.

In order to carry out an effective visualization, it is not sufficient to provide this to the user with one single instruction. As a rule, he needs a continuous input that can only be achieved by a suitably trained therapist or by animated visual timing. For this purpose, the contraction instructions of the on-screen animator are electronically linked to the urinary incontinence or core strength program of the rPMS. In this way, the user always receives the respective contraction instructions with millisecond accuracy at the intervention time (usually 8 sec) of the rPMS, since a visualization instruction would have a counterproductive effect during the pause time of the rPMS (4 sec).

Users can use the touchscreen to decide whether they prefer to hear a male or female voice or whether they want to see a male or female instructor and whether the timbre of the voice sounds very deep, bright, warm or dominant. The visualization is also available in the usual foreign languages.

Grab Handles 8 for Active Training

A purely mental "high mental effort training" can be strengthened if the user combines his mental contraction efforts with the attempt at muscle tensing. This can ideally be optimized if, by pulling or traction resistance by means of two grab handles 8 integrated into the arm rests on both sides, the user tensions both the abdominal and pelvic floor muscles and thus coordinates the affected muscles with regard to a physiological movement sequence. This active resistance training is only intended for core training, sarcopenia, in the case of stress incontinence and for spastic paralyzed users (paraplegia, stroke, multiple sclerosis).

LIST OF REFERENCE NUMBERS

1 Base frame
2 Seating arrangement
3 Seat surface
4 Backrest
5 Foot part
6 Armrest
7 Control panel
8 Grab handle
9 Light hood
10 Screen
11 Loudspeaker
12 Illuminating means
13 Microphone
14 Camera
15 Magnetic field applicator

The invention claimed is:

1. A device for magnetic field stimulation of a user's body tissue, comprising:
    an adjustable seating arrangement for the user, the adjustable seating arrangement comprising a seat surface, a backrest, a foot part, and two armrests,
    at least one magnetic field applicator for generating a pulsating magnetic field in a region of the seating arrangement,
    a control panel for adjusting one or more parameters of the pulsating magnetic field, including pulse duration, pulse frequency and pulse amplitude, and for adjusting settings for the seating arrangement,
    a display screen for displaying information,
    grab handles for active muscular resistance training of the user during use arranged in the region of the seating arrangement, a respective one of the grab handles extending transversely from and to a top surface of each of the two armrests in a direction opposite from the seat surface, and
    wherein the control panel is configured to manually and/or automatically adjust one or more of the parameters of the magnetic field and/or adjust the seating arrangement as a function of previously recorded individual information about the user, wherein the seating arrangement is adjusted automatically via the control panel based on a sitting or lying position previously saved and retrievable by the user.

2. The device according to claim 1, wherein the magnetic field applicator has one or more magnetic coils which are arranged in the seat surface and/or the backrest and/or the foot part of the seating arrangement.

3. The device according to claim 1, wherein the adjustment of the adjustable seating arrangement and/or adjustment of the parameters of the pulsating magnetic field is carried out automatically based on of the previously recorded individual information available about the user.

4. The device according to claim 1, further comprising a device for automatic recognition of the user.

5. The device according to claim 1, wherein the control panel is provided for entering and/or reading out individual information about the user, wherein the individual information comprises information about physical characteristics and/or health status of the user.

6. The device according to claim 5, wherein the individual information about a current user is compared with information from other users, and the parameters of the magnetic field for the current user are set by the control panel taking into account parameters previously set for the other users.

7. The device according to claim 1, wherein information about a mode of action of different adjustments of the pulsating magnetic field on the body tissue can be displayed on the display screen.

8. The device according to claim 1, further comprising a device for generating illumination and light effects is provided.

9. The device according to claim 1, further comprising an infotainment system for playing music, sounds, light and sound effects.

10. The device according to claim 1, further comprising a microphone for receiving voice information for voice control and/or for recognizing the user.

11. The device according to claim 1, wherein the control panel comprises a touch-sensitive display device.

12. The device according to claim 1, wherein the individual information recorded by the user is stored and evaluated in the device itself and/or in a control center.

* * * * *